United States Patent
Roche et al.

(10) Patent No.: US 7,163,518 B1
(45) Date of Patent: Jan. 16, 2007

(54) WALKING LEG SUPPORT

(75) Inventors: Martin Roche, Fort Lauderdale, FL (US); Mark Graham, Fort Lauderdale, FL (US)

(73) Assignee: RGPartnership LLP, Fort Lauderdale, FL (US)

( * ) Notice: Subject to any disclaimer, the term of this patent is extended or adjusted under 35 U.S.C. 154(b) by 244 days.

(21) Appl. No.: 10/824,125

(22) Filed: Apr. 14, 2004

Related U.S. Application Data

(60) Provisional application No. 60/512,402, filed on Oct. 20, 2003.

(51) Int. Cl.
- A61F 5/00 (2006.01)
- A43B 7/24 (2006.01)
- A63B 25/08 (2006.01)
- E04G 1/00 (2006.01)

(52) U.S. Cl. .............................. 602/11; 602/12; 36/142; 482/77; 182/230

(58) Field of Classification Search .................... 602/5, 602/11, 12, 16, 23, 27, 28, 29, 65, 66; 128/882; 36/140, 142, 110; 623/27, 46, 51; 482/75–77, 482/121; 182/221, 230

See application file for complete search history.

(56) References Cited

U.S. PATENT DOCUMENTS

| | | | | |
|---|---|---|---|---|
| 438,830 A | * | 10/1890 | Yagn | 482/77 |
| 1,575,847 A | * | 3/1926 | King et al. | 623/28 |
| 1,613,535 A | * | 1/1927 | Root | 623/28 |
| 2,206,234 A | * | 7/1940 | Murray | 602/11 |
| 2,899,685 A | * | 8/1959 | Bourcier De Carbon | 623/28 |
| 2,923,947 A | * | 2/1960 | Weighill | 623/28 |
| 3,058,120 A | * | 10/1962 | Smith et al. | 623/28 |
| 3,065,962 A | * | 11/1962 | Hoffmeister | 482/75 |
| 3,201,876 A | * | 8/1965 | Leumi | 36/7.5 |
| 3,278,946 A | * | 10/1966 | Godwin | 623/28 |

(Continued)

FOREIGN PATENT DOCUMENTS

FR    2594344    * 2/1986

(Continued)

OTHER PUBLICATIONS

McMaster-Carr Catalog p. 1829 Gas Springs.

Primary Examiner—Justine R. Yu
Assistant Examiner—Adam Brandt
(74) Attorney, Agent, or Firm—Alvin S. Blum

(57) ABSTRACT

Apparatus attaches to the leg at or below the knee to take the shock of walking off the foot and ankle. The foot is encased in a boot. Two spaced-apart tubes extend upward from a subfloor mounted below the boot. The boot is mounted for sliding up and down on the tubes. A pair of parallel elongate rods are attached at their upper ends to the upper portion of the leg at or below the knee, such that the lower ends of the rods are in the tubes. A spring, preferably a gas compression spring, is inserted into each tube so that the lower end of each rod compresses the spring as body weight is put on the subfloor in walking. The subfloor moves toward the boot as the springs are compressed, reducing some of the shock of walking and transferring forces to the leg. The rods may be attached to the leg by a cast, brace or orthosis.

20 Claims, 4 Drawing Sheets

U.S. PATENT DOCUMENTS

| | | | |
|---|---|---|---|
| 3,595,339 A * | 7/1971 | Ballard et al. | 182/230 |
| 3,660,920 A * | 5/1972 | Spina | 482/75 |
| 4,088,336 A * | 5/1978 | Chapel | 280/11.19 |
| 4,108,046 A | 8/1978 | Kiraly | |
| 4,567,678 A * | 2/1986 | Morgan et al. | 36/110 |
| 4,662,616 A | 5/1987 | Hennels | |
| 4,927,137 A * | 5/1990 | Speer | 482/76 |
| 5,011,136 A | 4/1991 | Rennex | |
| 5,133,419 A | 7/1992 | Barrington | |
| 5,183,036 A | 2/1993 | Spademan | |
| 5,263,691 A | 11/1993 | Sarghie | |
| 5,295,932 A * | 3/1994 | Rowan | 482/76 |
| 5,502,901 A * | 4/1996 | Brown | 36/28 |
| 5,509,874 A * | 4/1996 | Shih | 482/75 |
| 5,514,054 A * | 5/1996 | Rowan | 482/75 |
| 5,645,515 A * | 7/1997 | Armstrong et al. | 482/75 |
| 6,517,586 B1 * | 2/2003 | Lin | 623/28 |
| 6,581,919 B1 * | 6/2003 | Barefoot et al. | 267/132 |
| 6,589,194 B1 | 7/2003 | Calderon | |
| 6,648,803 B1 * | 11/2003 | Jay | 482/76 |
| 6,666,796 B1 * | 12/2003 | MacCready, Jr. | 482/51 |
| 2003/0196352 A1 * | 10/2003 | Bledsoe et al. | 36/110 |

FOREIGN PATENT DOCUMENTS

| | | | |
|---|---|---|---|
| FR | 2594344 A1 * | 8/1987 | |
| FR | 2594344 A1 * | 8/1987 | |

* cited by examiner

WALKING LEG SUPPORT

Applicants claim priority of provisional patent application Ser. No. 60/512,402, filed Oct. 20, 2003.

This invention relates to leg supports and more particularly to supports applied to the lower leg to facilitate walking for patients with leg and foot disabilities.

BACKGROUND OF THE INVENTION

Various devices are known such as casts, braces, cuffs, and splints that are designed to protect and stabilize the lower leg, ankle and foot when walking as they heal from injury or disorders such as diabetic ulcers.

U.S. Pat. No. 2,206,234 issued Jul. 2, 1940 to Murray discloses an invalid walking and apparatus that attaches to a cast or the leg below the knee that has a support plate for the foot. A cushioned member is suspended below the foot support. When body weight is put on the leg during walking, the cushioned member is forced up toward the foot support. Springs interposed between the cushioned member and the rest of the apparatus are compressed by the body weight. This cushions the forces on the foot and applies them first to the leg and then to the foot as the springs compress to prevent shock to the injured extremity. The apparatus affords little protection for the foot, and is not easily removed when not walking, or correctly reattached when needed.

SUMMARY OF THE INVENTION

It is accordingly an object of the invention to provide apparatus with a portion that attaches to a cast, brace, or orthotic on the leg at or below the knee. It is another object that the apparatus provide a boot portion for protecting the foot and securing the base of the cast or orthosis. It is another object that the apparatus provide a subfloor portion spaced below the boot portion, toward which the boot portion is gradually forced when body weight is applied to the leg during walking to reduce shock and load to the lower leg, foot, and ankle. It is yet another object that the apparatus provide means for adjusting the degree of spring resistance to movement of the boot portion toward the subfloor by easy replacement of certain spring members. It is yet another object that the apparatus provide means for easily removing and replacing the majority of the apparatus when not walking without the need for adjustment. It is yet another object that the apparatus provide means for wholly or partially unloading the patient's weight and ground reaction forces by transfer of the load to the upper calf and tibia. It is yet another object that resilient members dampen and help dissipate these forces. It is yet another object to provide spring propulsion of the leg through the gait cycle for enhanced ambulation.

These and other objects, features, and advantages of the invention will become more apparent when the detailed description is studied in conjunction with the drawings in which like elements are designated by like reference characters in the various drawing figures.

DETAILED DESCRIPTION OF PREFERRED EMBODIMENTS

Figure 1:
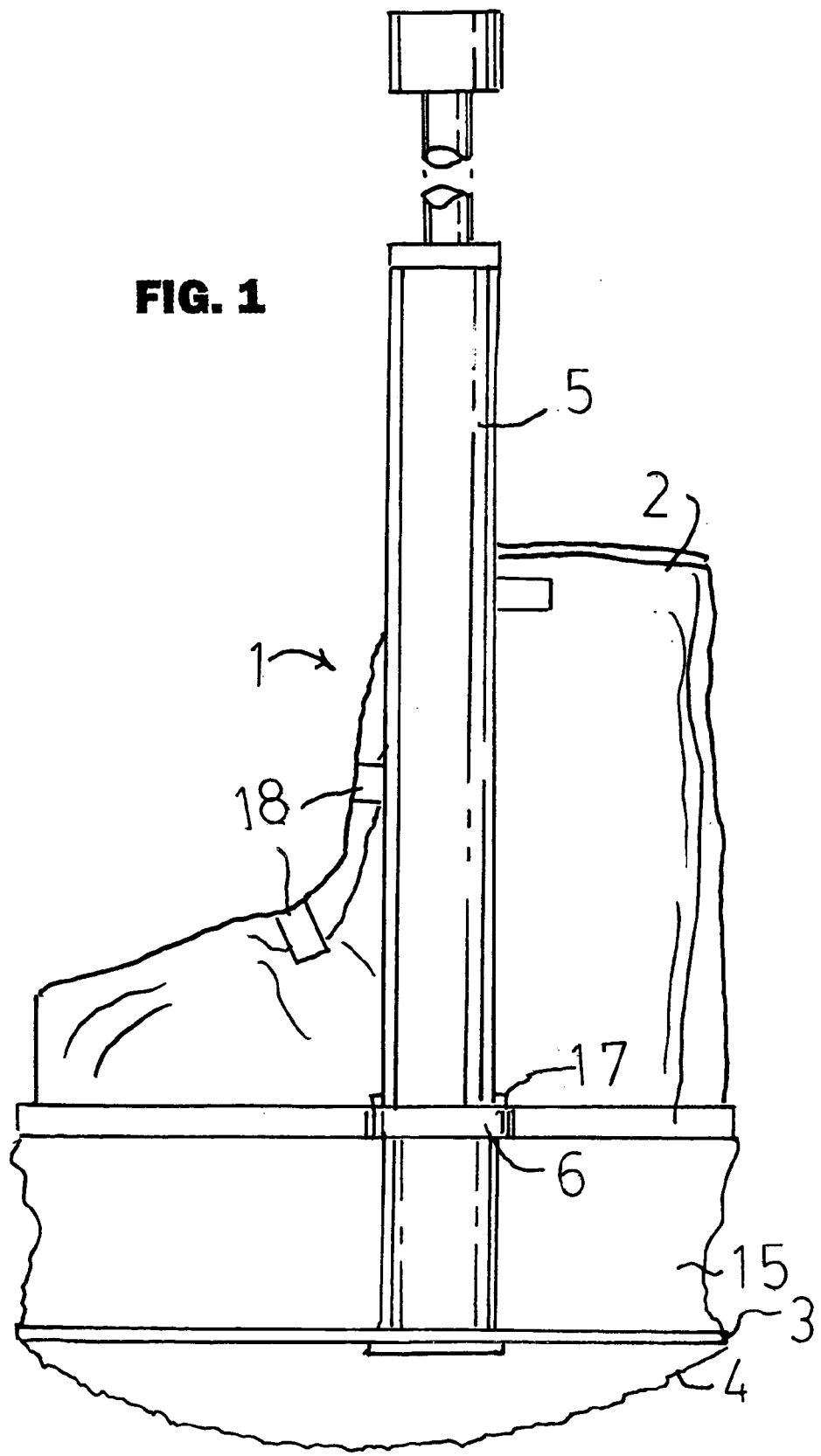
FIG. 1 is a side elevation view of the support.
Figure 2:
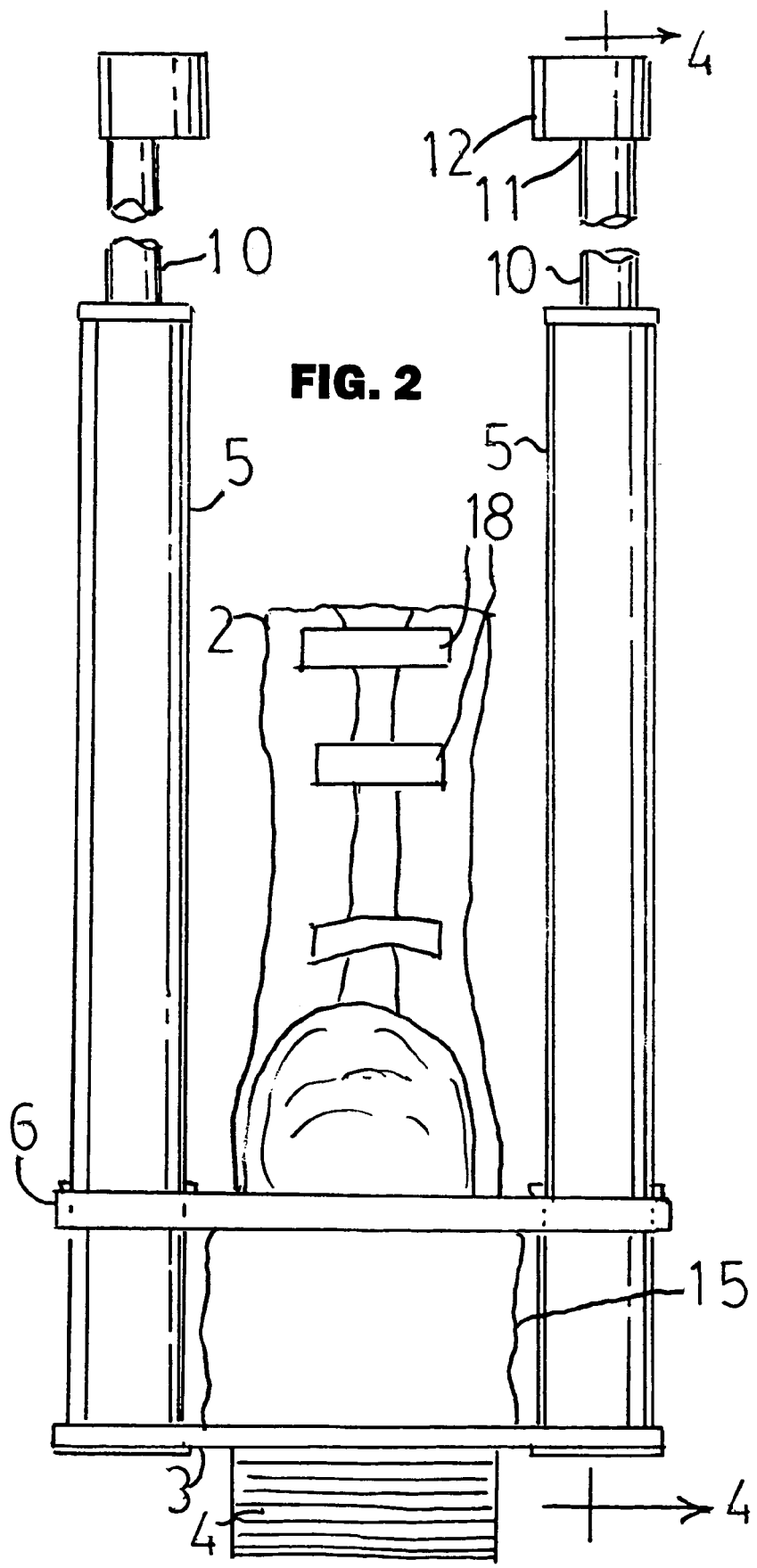
FIG. 2 is a front elevation view of the support.
Figure 3:
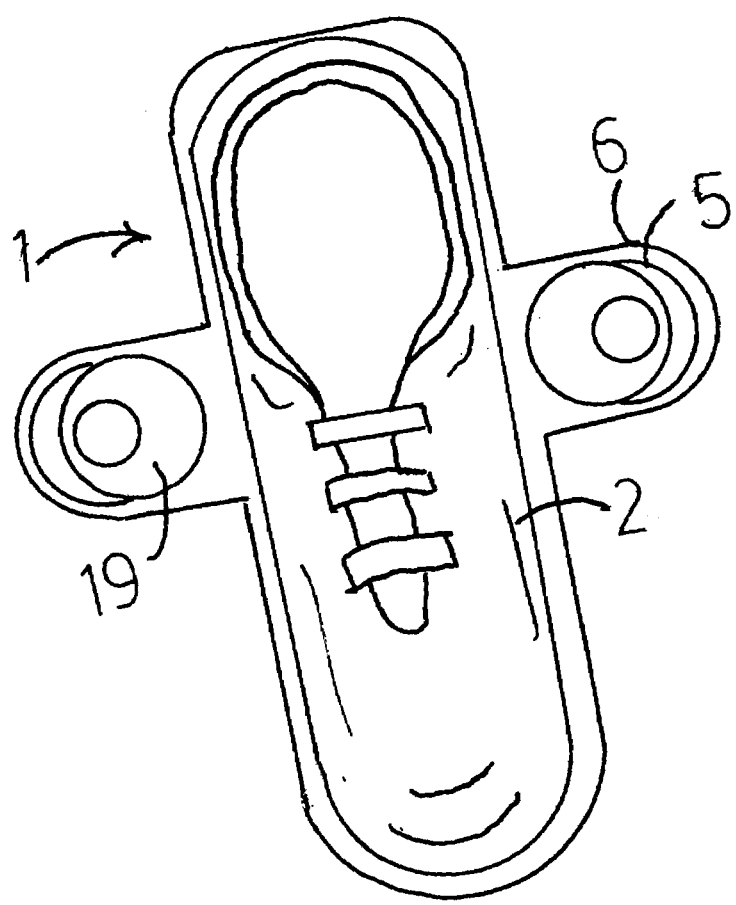
FIG. 3 is a top view of the support.
Figure 4:
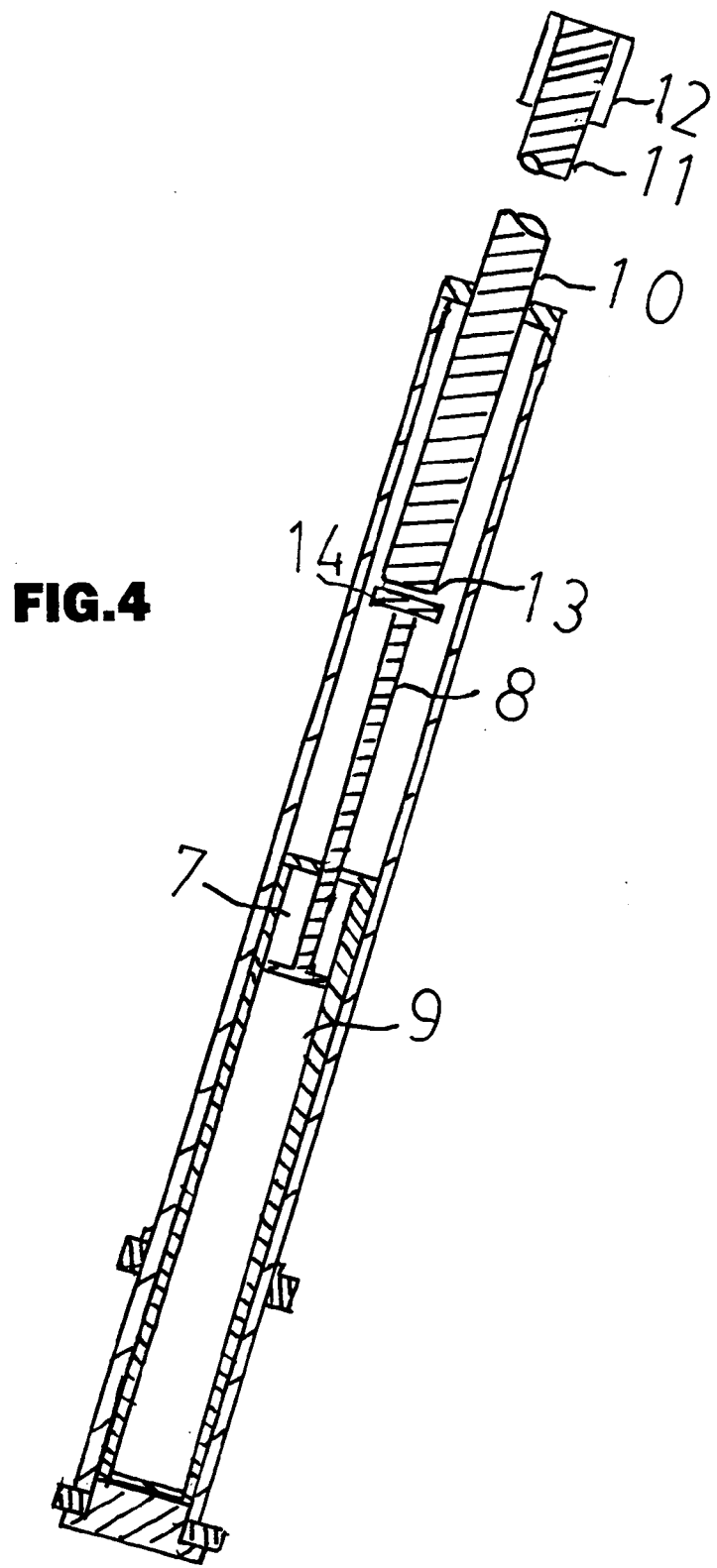
FIG. 4 is a sectional view taken through line 4—4 of FIG. 2.

Referring now to the drawing Figures, the walking support 1 of the invention has a boot portion 2 for removably receiving the foot of a person who is in need of some means of reducing the shock received to the foot in walking. This may include people suffering from diabetic foot ulcers, fractures of the bones of the lower leg, foot, or ankle, for example. The boot portion 2 may be supplied with fasteners well known in the art, such as the hook and loop fasteners 18 shown. The leg may be in a cast, orthosis, brace, or the like. A subfloor portion 3 positioned below the boot portion has a resilient arcuate or rocker bottom surface 4 that hits the pavement first when walking. A pair of elongate tubular members 5 are affixed to the subfloor portion 3 and extend upward therefrom. The boot portion is slidably mounted by mounting means 6 so as to be freely movable up and down on the tubular members 5. A pair of elongate elements 10 have a first end 11 provided with means 12 for mounting on the leg below the knee, such as by being incorporated into a cast. They may also be strapped to a leg or a brace or orthosis, for example. They are provided with eccentric termini 19 so that they may be rotated to adjust their spacing to be parallel and fit into the tubular members 5. The second end 13 of each element 10 is constructed for being slidably received within the tubular member 5 and onto the top 14 of a spring element 7. The compression spring element 7 includes a piston 8 in a pressurized gas cylinder 9. This is freely movable and removable from the tubular members. A pressurized nitrogen gas spring has been found to be useful, but other compression spring elements such as metal coil springs and elastomeric springs (not shown) may be substituted if desired. Springs with various compression forces may be supplied so that one suitable for a particular application may be simply dropped into the member 5 without the use of tools. Many different spring forces may be tried until one suited to the application is found. With changes in the patient's condition, it may be useful to change springs.

When the walking patient's weight is put on a leg, the bottom 4 of the subfloor hits the pavement first. The arcuate shape facilitates the walking action. The body weight is transmitted through the elements 10, to the springs 7, and then to the subfloor portion 3. But the spring action causes the piston 8 to compress the gas in the cylinder 9, slowing the transmission of all of the force to the subfloor while allowing the boot portion to reach the subfloor portion. If the spring selected is strong enough, and the patient light enough the boot portion may never reach the subfloor portion. This may be desirable in the early stages of some therapy. It has been found that the spring extending when weight is removed lifts the foot and facilitates walking.

A resilient structure such as a spring or foam 15 may be interposed between the boot portion and the subfloor portion to prevent the entry of foreign items and provide further load damping. The subfloor portion may be recessed to receive a portion of the resilient structure 15. Everything except the elongate elements may be removed by simply unfastening the boot and lifting foot and the elements out of the members 5, when not needed. The reverse process reassembles the apparatus for walking. A stop 17 limits the upward motion of the boot portion on the members 5.

While we have shown and described the preferred embodiments of our invention, it will be understood that the invention may be embodied otherwise than as herein specifically illustrated or described, and that certain changes in form and arrangement of parts and the specific manner of practicing the invention may be made within the underlying idea or principles of the invention.

What is claimed is:

1. A walking support for a leg, the support comprising:
   a) a boot portion for receiving a foot;
   b) a subfloor portion;
   c) a pair of elongate tubular members affixed to, and extending upwards from, the subfloor portion;
   d) the boot portion slidably mounted on the exterior of the elongate tubular members for free vertical translatory motion thereon;
   e) a spring element freely movable within each elongate tubular member; and
   f) a pair of elongate elements, each elongate element having a first end provided with means for mounting on a leg below the knee, and a second end constructed for being slidably received within the elongate tubular member atop the spring element, so that when the first ends are mounted on the leg and the foot is in the boot, walking forces will be absorbed by the second ends compressing the spring elements.

2. The walking support according to claim 1 in which the spring elements are gas springs.

3. The walking support according to claim 1 in which the spring elements are elastomeric springs.

4. The walking support according to claim 1 in which the spring elements are coil springs.

5. The walking support according to claim 1 constructed so that the elongate elements may be removed from the remainder of the apparatus by unfastening the boot from the foot and lifting them from the elongate tubular members, and the support may be reassembled without adjustment by inserting the foot in the boot and the elongate elements in the elongate tubular members.

6. The walking support according to claim 1 further comprising a resilient structure interposed between the boot portion and the subfloor portion.

7. A walking support for a leg, the support comprising:
   a) a boot portion for receiving a foot;
   b) a subfloor portion;
   c) a pair of elongate tubular members affixed to, and extending upward from, the subfloor portion;
   d) the boot portion slidably mounted on the exterior of the elongate tubular members for free vertical translatory motion thereon;
   e) a gas spring freely movable within each elongate tubular member; and
   f) a pair of elongate elements, each elongate element having a first end provided with means for mounting on a leg below the knee, and a second end constructed for being slidably received within the elongate tubular member atop the gas spring element, so that when the first ends are mounted on the leg and the foot is in the boot, walking forces will be absorbed by the second ends compressing the gas springs.

8. The walking support according to claim 7 constructed so that the elongate elements may be removed from the remainder of the apparatus by unfastening the boot from the foot and lifting them from the elongate tubular members, and the support may be reassembled without adjustment by inserting the foot in the boot and the elongate elements in the elongate tubular members.

9. The walking support according to claim 8 further comprising a resilient structure interposed between the boot portion and the subfloor portion.

10. The walking support according to claim 7 further comprising a resilient structure interposed between the boot portion and the subfloor portion.

11. A walking support for a leg, the support comprising:
    a) a boot portion;
    b) a subfloor portion;
    c) a resilient structure interposed between the boot portion and the subfloor portion to keep the area therebetween free of foreign items;
    d) a pair of elongate tubular members affixed to, and extending upwards from, the subfloor portion;
    e) the boot portion slidably mounted on the exterior of the elongate tubular members for free vertical translatory motion thereon;
    f) a gas spring element freely movable within each elongate tubular member;
    g) a pair of elongate elements, each elongate element having a first end provided with means for mounting on a leg below the knee, and a second end constructed for being slidably received within the elongate tubular member atop the gas spring element so that the elongate elements may be removed from the remainder of the apparatus by unfastening the boot from the foot and lifting them from the elongate tubular members, and the support may be reassembled without adjustment by inserting the foot in the boot and the elongate elements in the elongate tubular members; and
    h) the gas springs being freely replaceable when the elongate elements are removed from the elongate tubular elements.

12. The support according to claim 11 in which the subfloor portion has an arcuate bottom surface.

13. The support according to claim 11 further comprising adjustment means for orienting the elongate tubular elements so that they are parallel to one another.

14. A walking support for a leg, the support comprising:
    a) a boot portion;
    b) a subfloor portion;
    c) a resilient structure interposed between the boot portion and the subfloor portion;
    d) a pair of elongate tubular members affixed to, and extending upwards from, the subfloor portion;
    e) the boot portion slidably mounted on the exterior of the elongate tubular members for free vertical translatory motion thereon; and
    f) a pair of elongate elements, each elongate element having a first end provided with means for mounting on a leg below the knee, and a second end constructed for being slidably received within the elongate tubular member atop the gas spring element so that the elongate elements may be removed from the remainder of the apparatus by unfastening the boot from the foot and lifting them from the elongate tubular members, and the support may be reassembled without adjustment by inserting the foot in the boot and the elongate elements in the elongate tubular members.

15. The support according to claim 14 in which the subfloor portion has a resilient arcuate bottom surface.

16. The support according to claim 15 further comprising adjustment means for orienting the elongate tubular elements so that they are parallel to one another.

17. The support according to claim 14 further comprising adjustment means for orienting the elongate tubular elements so that they are parallel to one another.

18. The support according to claim 14 in which the resilient structure includes compression springs.

19. The support according to claim 18 in which the subfloor portion has a resilient arcuate bottom surface.

20. The support according to claim 18 further comprising adjustment means for orienting the elongate tubular elements so that they are parallel to one another.

* * * * *